United States Patent [19]

Skottegard

[11] Patent Number: 4,807,712
[45] Date of Patent: Feb. 28, 1989

[54] SELF-PROPELLED CARRY-ALL TABLE FOR INVALIDS

[76] Inventor: Christopher Skottegard, 357A Nature Ct., San Jose, Calif. 95123

[21] Appl. No.: 87

[22] Filed: Mar. 23, 1987

[51] Int. Cl.$^4$ .................... B62D 51/04; B62D 11/02
[52] U.S. Cl. .................... 180/6.5; 180/19.1; 280/35; 280/47.11; 280/79.11; 446/454; 901/1
[58] Field of Search .................... 180/19.1, 131, 19.3, 180/167, 168, 169, 907, 6.26, 6.28, 6.48, 6.5, 6.66, 333; 280/79.1 A, 35, 47.11, DIG. 5; 414/921; 901/1; 446/454 X, 31, 451, 460

[56] References Cited

U.S. PATENT DOCUMENTS

| | | | |
|---|---|---|---|
| 2,574,897 | 11/1951 | Tantimonaco | 280/79.1 A X |
| 3,173,512 | 6/1964 | Carpezzi | 280/35 |
| 3,731,756 | 5/1973 | Hajec | 280/DIG. 5 X |
| 3,802,524 | 4/1974 | Seidel | 180/6.5 |
| 3,812,929 | 5/1974 | Farque | 180/167 |
| 4,483,405 | 11/1984 | Noda et al. | 180/6.5 |
| 4,592,562 | 6/1986 | Strautnieks et al. | 414/921 X |
| 4,627,511 | 12/1986 | Yajima | 180/167 |
| 4,657,267 | 4/1987 | Jaumann et al. | 280/47.11 |

FOREIGN PATENT DOCUMENTS

2172213 9/1986 United Kingdom ................ 446/454

Primary Examiner—David M. Mitchell
Assistant Examiner—Charles R. Watts
Attorney, Agent, or Firm—Donald C. Feix; Thomas M. Freiburger

[57] ABSTRACT

A self-propelled table for carrying and/or lifting/lowering objects for invalid people having a hollow plastic upper enclosure which is padded at the edges and upon the surface of which contains anti-slip recesses and a joystring assembly. The lower portion of this assemblage is attached to a vertically mounted, telescoping tubular assembly which may be either fixed or supplemented with a motor-power assembly with which to adjust the height-away-from-the-floor of the uppermost serving surface. The bottom of the tubular assembly is attached to the upper portion of a hollow plastic lower enclosure which contains wheels, motors, batteries, and electronic circuits to translate the electronic signals from the joystring into meaningful wheel motions. Pulling the free end of the joystring causes the invention to propel itself and it's load in the same direction that the joystring was pulled; thereby providing handicapped people with the ability to perform simple tasks unassisted.

7 Claims, 14 Drawing Sheets

PIN OUTLINES

| TYPE | U1<br>LM555 | U2<br>LM556<br>(1) | U3<br>LM556<br>(2) |
|---|---|---|---|
| GROUND | 1 | 7 | 7 |
| TRIGGER | 2 | 8 | 6 |
| OUTPUT | 3 | 9 | 5 |
| RESET | 4 | 10 | 4 |
| VOLTAGE CONTROL | 5 | 11 | 3 |
| THRESHOLD | 6 | 12 | 2 |
| DISCHARGE | 7 | 13 | 1 |
| +DC VOLTAGE | 8 | 14 | 14 |

SELF-PROPELLED CARRY-ALL TABLE FOR INVALIDS

BACKGROUND OF THE INVENTION

This invention relates in general to the cane, crutch, and walker prior art and in particular to prior art wheeled legs and the attachable trays and baskets for these inventions. And insofar as this prior art intends to help walker-bound invalid people achieve a minimum degree of self-sufficiency, it nevertheless fails for a significant number of these people because they lack the basic strength and control necessary to utilize these inventions as they were intended to be used.

For example, a significant number of walker-bound people are unable to perform the simple task of carrying a prepared meal from a refrigerator or stovetop to a dining room table without either spilling the meal or by doing so with great difficulty. This is principally due to the fact that these people must use both hands to handle the walker and, thus, they have no free hands with which to transport their meal. Similarly, people who are dependent on canes, crutches, or other assistive devices experience comparable, although somewhat lesser, degrees of difficulties in this situation.

Continuing with the example, walker-bound people might decide to modify their walkers to include prior art front wheels in place of front legs in addition to a tray or basket. Hence, with these modifications, a walker-bound person is theoretically capable of transporting prepared meals. In practice however, a large percentage of walker-bound people spill their meals because they lack the strength and control necessary to keep from jerking or 'hopping' their walker. Similarly, a significant number of walker-bound invalids don't do their own laundry because, even with the aforementioned modifications to their walkers, they lack the strength necessary to push these relatively heavy loads.

Thus, although crutch-, cane-, and/or walker-bound people want to feel useful and self-sufficient, they nevertheless tend to remain dependent upon other, non-invalid people to provide many basic, home health care services for them. The social and financial burden implicit with the need for these personal services can often be in excess of what many of these handicapped people can reasonably afford.

SUMMARY OF THE INVENTION

The invention provides walking-assistance-dependent, handicapped people with the ability to perform simple household tasks conveniently and inexpensively, with minimal or no additional assistance. The invention accomplishes this by providing a unique, effortlessly controlled, self-propelled, adjustable-height table which carries desired objects while following immediately behind a handicapped person as this person goes about performing simple household tasks.

The present embodiment of the invention is comprised of two components separated by a common vertical assembly. The upper component of the invention is comprised of a serving surface, a padded assembly along the perimeter of this surface, a hollow body, and certain electronic instruments and circuitry, including a unique joystring instrumentation assembly developed especially for this and similar applications.

The common extension assembly physically connects the upper component of the complete service table assembly to the lower component while it also contains an electro-motive apparatus which is used to adjust the height of the serving surface.

Finally, the lower component of the service table assembly is comprised of a hollow body within which is housed the motor/wheel assembly, the rechargable battery, and a unique electronic circuit which utilizes the information provided by the joystring assembly to control the movement of the service table in such a manner as to be both self-navigating and capable of transporting both heavy loads and delicate loads without spilling.

In operation, the free end of the joystring is either pulled directly by the operator of the invention or tied directly to a convenient location on the operators' walker, wheelchair, cane, or whatever. Moving the free end of the joystring causes the invention to propel itself in such manner as to follow the subject operator. The height of the upper surface of the invention is adjusted by temporarily depressing the rocker-arm type switch. As an example of actual use, therefore, the height could initally be set to that of a stovetop or refrigerator, at which point the operator of the invention loads the service table with prepared foods. The invention is then propelled to a desired location at which point the height is lowered to be more convenient for dining while seated.

Other embodiments utilizing the principal features of this invention immediately suggest themselves to persons skilled in the art. These embodiments may be based upon additional uses of the invention as, for example, a self-propelled ambulatory device. Other embodiments may range in scope from children's toys to industrial-quality tools. Accordingly, it is intended to be understood that many embodiments thereof will suggest themselves without departing from the spirit and scope of this invention.

BRIEF DESCRIPTION OF THE DRAWINGS

The present invention will be described in detail by way of illustrative example with reference to the accompanying drawings, in which;

FIG. 3 is the schematic representation and pin outlines of certain of the electronic components used in FIG. 12.

DETAILED DESCRIPTION OF THE INVENTION

During the course of this description like numbers will be used to identify like elements according to the different figures which illustrate the invention.

Figure 1:
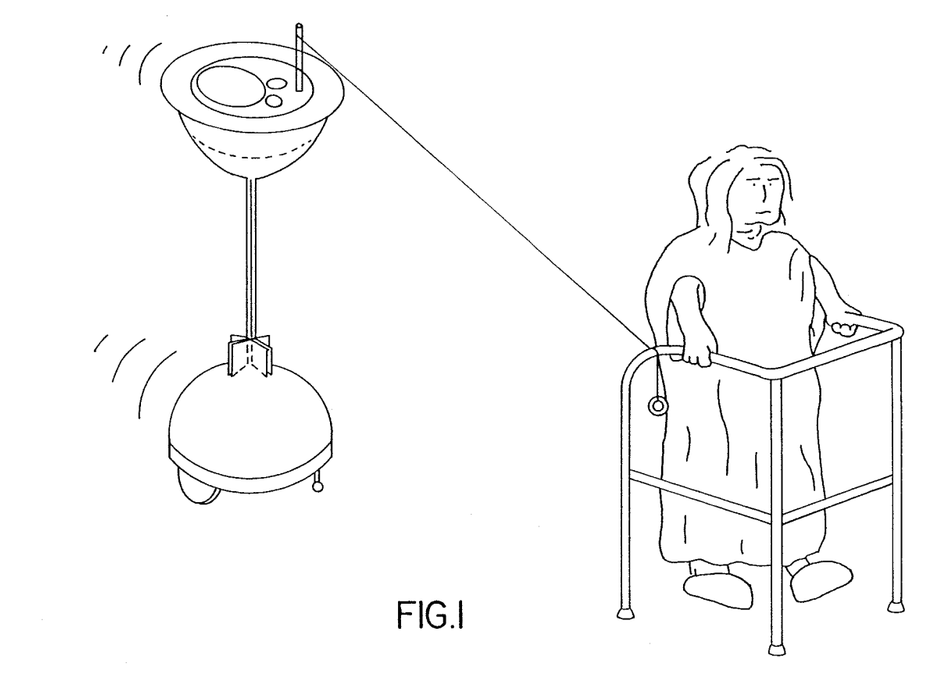
FIG. 1 is a perspective view of the self-propelled, self-navigating service table being used by an invalid person.

FIG. 1 shows an invalid person using the invention in conjunction with a prior art walker.

Figure 2:
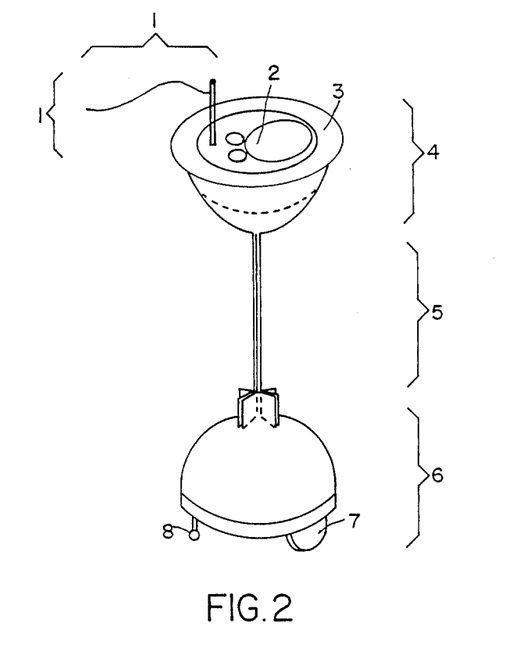
FIG. 2 is an enlarged perspective view of the self-propelled, self-navigating service table according to an embodiment of the present invention.

Referring to FIG. 2, some of the primary elements of the preferred embodiment include the joystring controller assembly 1, the serving surface 2, the padded cushion assembly 3, the top half assembly 4, the extension tube assembly 5, the bottom half assembly 6, the drive wheels 7, and the casters 8. The present embodiment of the invention can carry loads of up to 75 pounds and accelerates and decelerates gradually to a maximum speed of approximately 1 foot per second.

Figure 3:
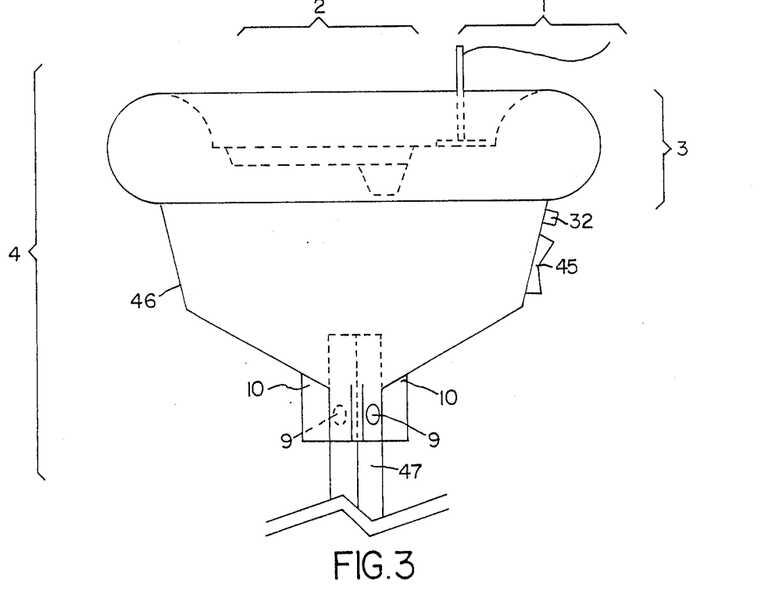
FIG. 3 is a side view of the top half of the service table of FIG. 2.

Referring to FIG. 3, the relative positions of certain components of the top half assembly 4 are shown. The joystring controller assembly 1 is shown extending vertically from the serving surface 2. The padded cushion assembly 3 extends beyond, above, the below the perimeter of the top of the top-half assembly 4. The electrical connector for the battery charger 32 is located below the padded cushion 3 and the rockerarm-type momentary switch 45 is located immediately below this. The upper section of the extension tube 47 is secured to the upper assembly coverplate 46 by two rivets inserted through holes 9 and extending into the interior surface of the upper extension tube 47. The upper brackets 10, which are adhered to the upper half assembly coverplate 46, provide structural support at this interface.

Figure 4:
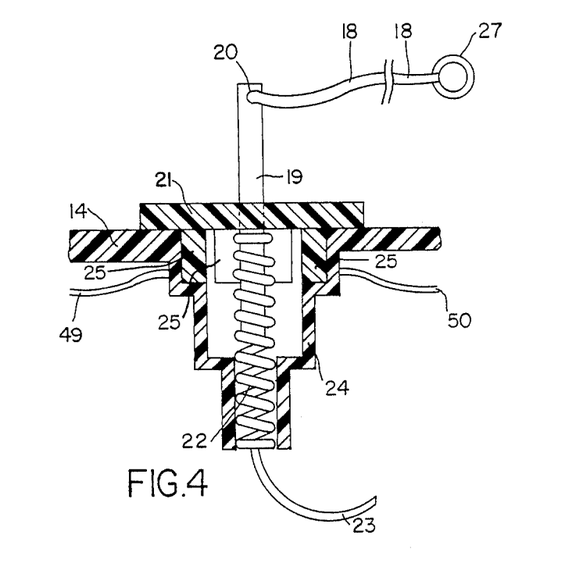
FIG. 4 is a sectional side view of the joystring instrumentation mechanism.

FIG. 4 presents the joystring controller assembly 1 which has been developed specifically for application to the present embodiment and for similar applications where it is desirable to have a machine follow a human operator. The joystring controller assembly 1 is unique in that it is useful for radii of up to several feet, rather than being limited to the inch or so characteristic of joysticks. Thus, a joystring indicates a desired direction from a remote distance which is much greater than what is available from prior art joysticks.

The grip ring 17 is tied to one of the free ends of the elastic string 18. The other end of the elastic string 18 is adhered to the top of the joystring post 19. At the middle of the joystring post 19 is adhered a slip-plate 21 which slides freely over the non-recessed serving surface 14. The joystring post 19 extends through the center of the top of the spring 22 and the bottom of the post 19 is adhered to the spring 22. The bottom of the spring 22 is secured to the joystring housing 24 and makes electrical contact with the centertap wire 23.

Figure 5:
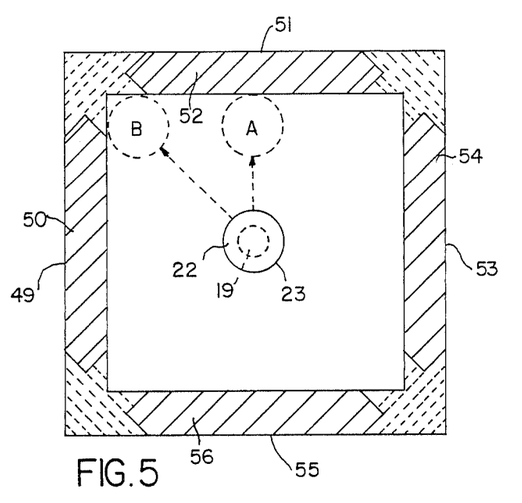
FIG. 5 is a cross-sectional top view of the joystring instrumentation mechanism taken along line V—V of FIG. 4.

As shown in FIG. 5, the contact plate representing forward motion 52 is electrically connected (soldered) to wire 51. Similarly, the contact plate representing right-hand motion 54 is soldered to wire 53, the contact plate representing reverse motion 56 is soldered to wire 55, and the contact plate representing left-hand motion 50 is soldered to wire 49. Normally, the spring 22 remains in open circuit with respect to the contact plates 50, 52, 54, and 56 and, thus, wire 23 is not normally electrically connected to any of the remaining wires 49, 51, 53, or 55. In operation, however, pulling the grip ring 17 with a minimal amount of force causes the spring 22 to bend and make electrical contact with one or two of the electrical contacts 50, 52, 54, and 56. Thus, when the grip ring 17 is pulled, wire 23 makes a closed electrical contact with one or two of the four wires 49, 51, 53, and 55. The dashed circles exemplify this process. In case A, wires 51 and 23 are electrically connected because the spring 22 has bent forward and has made electrical contact with the electrical contact representing forward motion 52. In case B, wires 49, 51, and 23 make simultaneous electrical contact because pulling the grip ring 17 bends the spring 22 to the point where the spring 22 makes simultaneous electrical contact with the electrical contact representing forward motion 52 and the electrical contact representing motion to the left 50.

Figure 6:
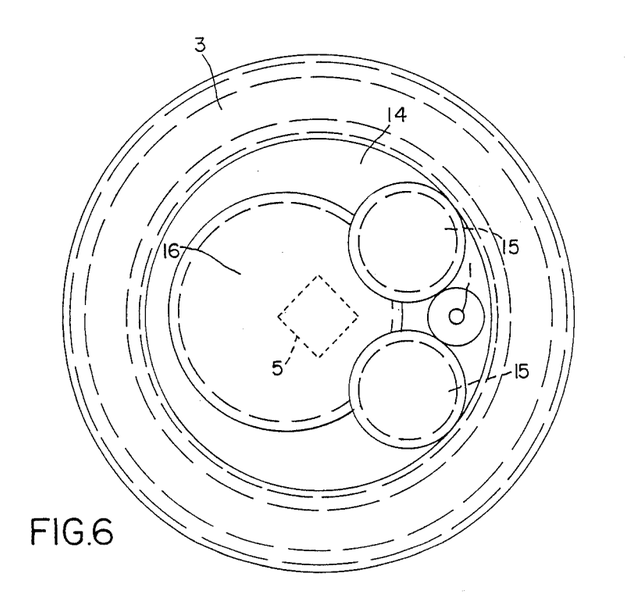
FIG. 6 is the top view of FIG. 2.

The top view provided by FIG. 6 illustrates the relative positions of the joystring controller assembly 1 to the padded cushion assembly 3, the food recess 16, beverage recesses 15, and the padded cushion assembly 3.

Figure 7:
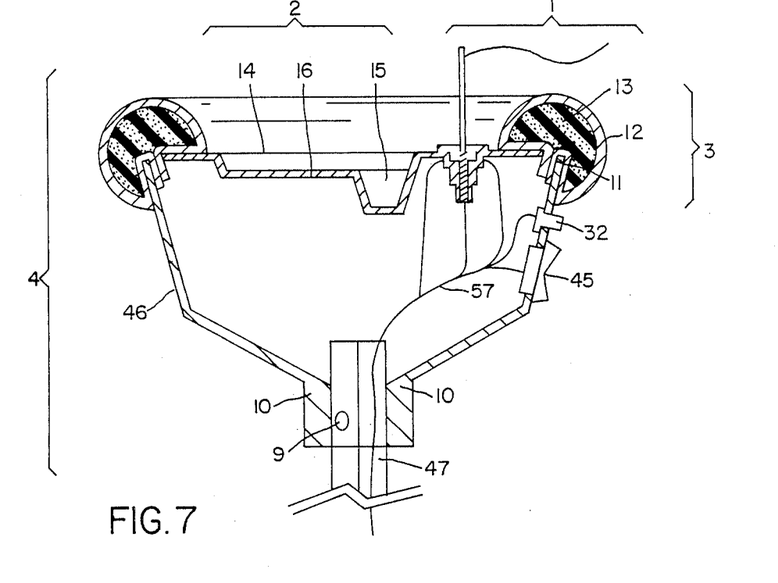
FIG. 7 is a sectional side view of FIG. 3.

Referring to FIG. 7, the relative positions of the joystring controller assembly 1 to the padded cushion assembly 3, the food recess 16, beverage recesses 15, and the padded cushion assembly 3 are shown in a cross-sectional view. In addition, the upper assembly 4 is shown to be partially comprised of the serving surface 2 and the top half assembly coverplate 46, which are adhered to each other at point 11. The padded cushion assembly 3 is comprised of the surface fabric 12, which is adhered to the exterior of the foam cushion 13, and again adhered at point 11, which extends along the entire perimeter of the serving surface 2. The serving surface 2 is comprised of the exterior portion of the serving surface 14, the two recesses for securing beverage containers 15, and the recess 16 for securing other foodstuffs. The placement of the joystring controller assembly 1 relative to the electrical connector for the battery charger 32, and the rocker-arm-type momentary DPDT switch 45 is also shown. The bundled electrical wires 57 originating from the joystring controller assembly 1, the electrical connector for the battery charger 32, and the rocker-type momentary DPDT switch 45 are fed to the bottom assembly 6 via the hollow interior of the extension tube assembly 5.

Figure 8:
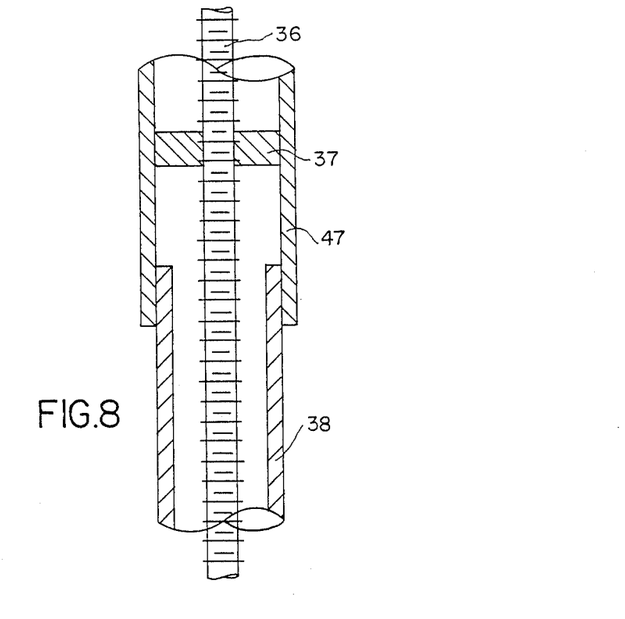
FIG. 8 is a cross-sectional side view of the extension tube according to another embodiment of the present invention.

FIG. 8 illustrates the mechanism which is used to adjust the height of the upper assembly 4 relative to the lower assembly 6. The inner diagonal of the upper section of the extension tube 5 is slightly larger than the outer diagonal of the lower section of the extension tube 38. Thus, the upper extension tube 5 slides over the lower extension tube 38. Both upper and lower section tubes have a squared profile to keep the two sections from rotating relative to each other. Secured to the interior of the upper extension tube 5 is a threaded nut 37 through which passes a long, matched-threaded bolt 36. By rotating the threaded bolt 36, the upper extension tube 5 is forced to slide vertically over the lower extension tube 38.

Figure 9:
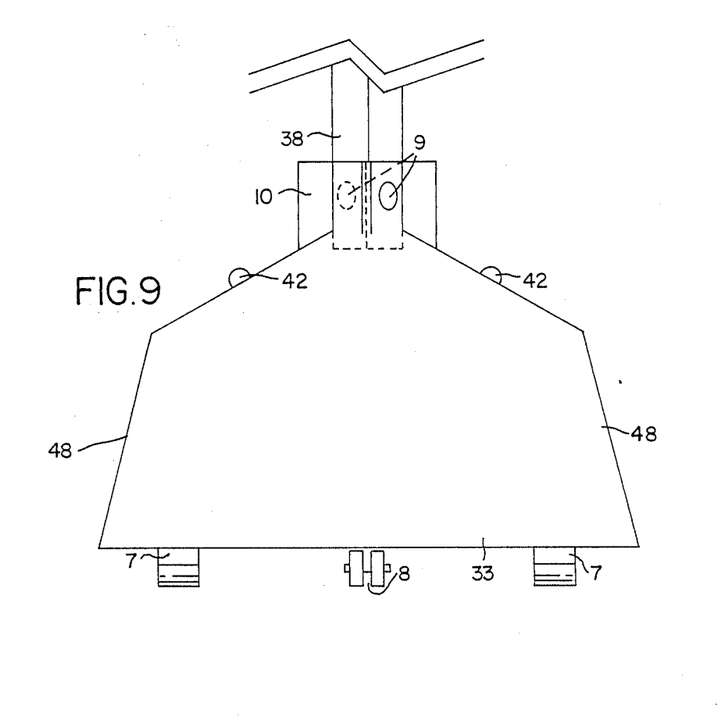
FIG. 9 is a side view of the bottom half of the service table of FIG. 2.

Referring to FIG. 9, the lower section of the extension tube 38 is secured to the lower assembly coverplate 48 by two rivets inserted through holes 27 and extending into the interior surface of the lower extension tube 38. The lower brackets 26, which are adhered to the bottom half assembly coverplate 48, provide supplementary structural support at this interface.

Figure 10:
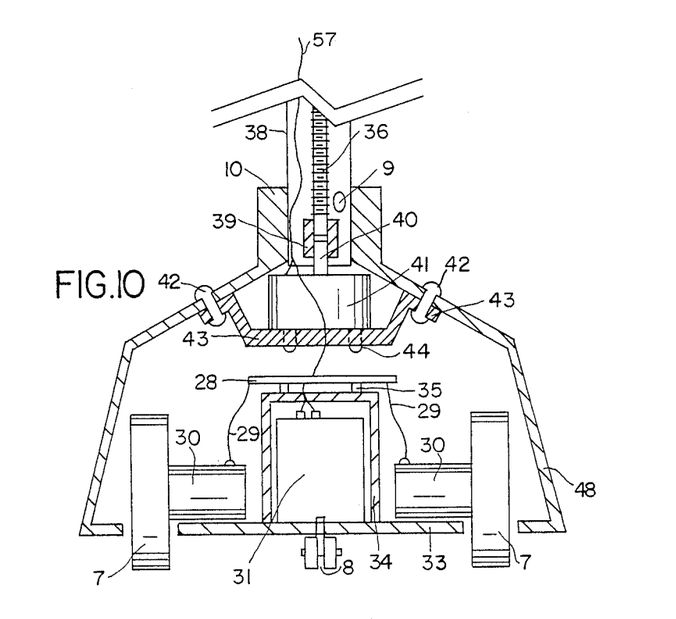
FIG. 10 is a sectional side view of FIG. 9.

Referring to FIG. 10, the bundle of wires 57 feeds through the bottom opening of the lower section of the extension tube 38 and terminate on the circuit board 28. Wires 29 also extend from the circuit board 28 to the drive motors 30, the battery 31, and the extension tube drive motor 41. Screws 44 are used to secure the mounting plate 43 to the extension tube drive motor 41 and rivets 42 secure the mounting plate 43 to the lower assembly coverplate 48. The extension tube drive motor's rotating shaft 40 is linked to the threaded shaft 36 via a keyed bushing 39. This keyed bushing 39 contains setscrews to maintain the integrity of this linkage.

The circuit board 28 is mounted on top of the battery casing 34 via the mounting posts 35. The battery casing 34 is secured to the baseplate 33, the drive motors 30 are directly coupled to the drive wheels 7 via bushings and setscrews, and each of these two motor/wheel assemblies is secured to the baseplate 33. The baseplate 33 is secured to the bottom half assembly coverplate 48 along the perimeter of this interface.

Figure 11:
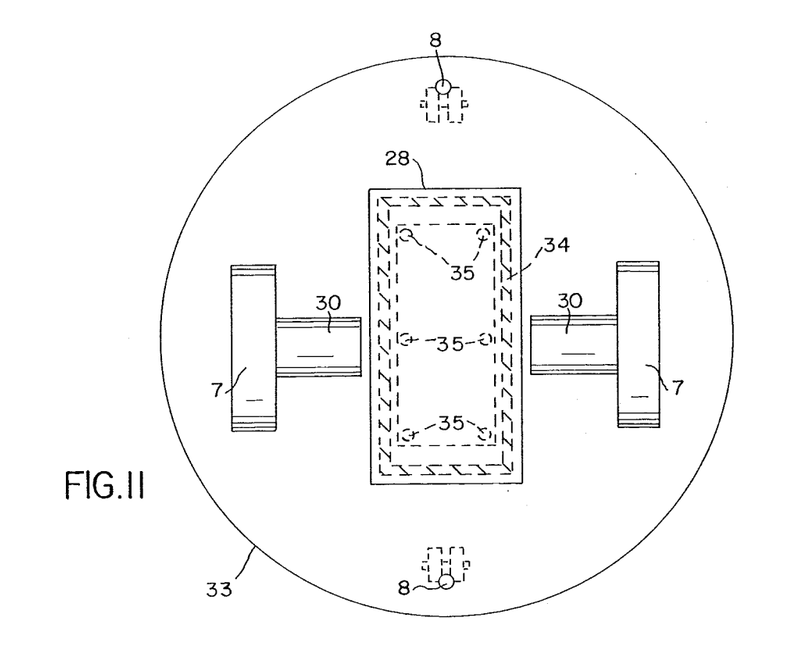
FIG. 11 is the top view of the exposed bottom half assembly of the service table of FIG. 2.

Referring to FIG. 11, the lower assembly coverplate 48 has been removed to expose the top view of the baseplate 33, the circuit board 28, the mounting posts 35, the battery casing 34, each of the two drive motors 30, the two drive wheels 7, and the two casters 8.

Figure 12:
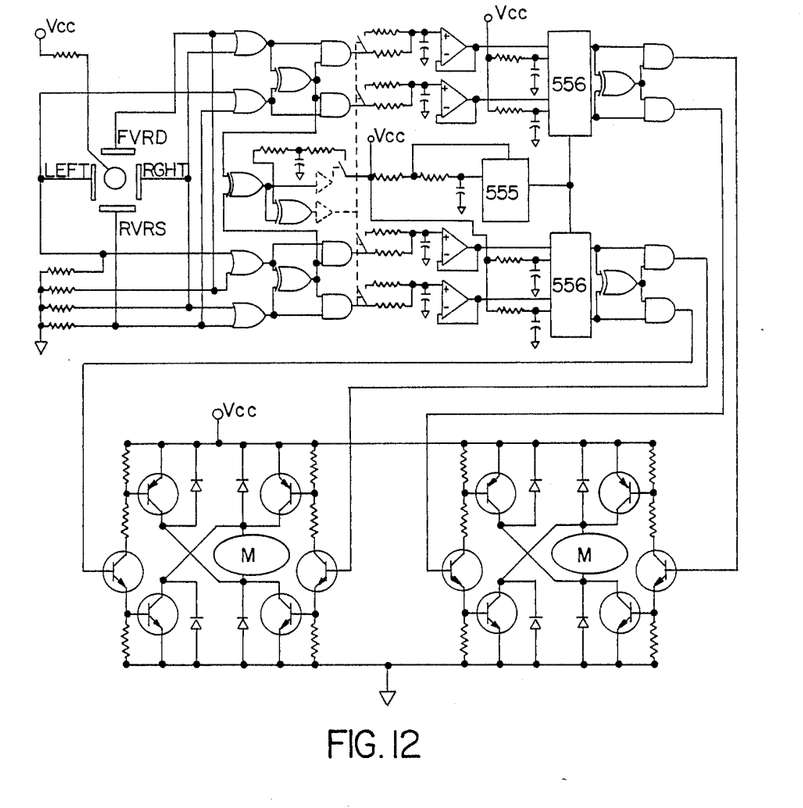
FIG. 12 is the schematic representation of the circuit board used in the self-propelled, self-navigating service table.

Referring to FIG. 12, the schematic representation of the joystring assembly 1 presented on the left of FIG. 12. This representation of the joystring assembly 1 is characterized by the four wires 51, 53, 55, and 49 which represent the positions of forward F, right R, reverse RS, and left L, respectively. When the spring 22 of the joystring assembly is not activated, the voltage potential on each of these four terminals is set to zero via the four individual grounding resistors R-low. As discussed earlier, pulling the grip ring 17 activates the joystring and brings the subject terminals from the ground state to the voltage V=Vcc X R-high/R-low. This voltage V must exceed the minimum activation voltage of the OR gate inputs.

The two XOR gates connected directly to the outputs of the four OR gates and to the inputs of the four AND gates U4 assure that a maximum of one of the two lines for each motor is activated. This is necessary to avoid the excessive current drain that would occur to the battery should both lines to either motor be brought high simultaneously.

Early versions of the embodiment connected the outputs of the AND gates U4 to the respective outputs of the AND gates U5 and eliminated all of the intermediate circuitry. This subject circuit has the effect of turning the motors on and off instantaneously. If tests had not showed that, under certain circumstances, foodstuffs might have been spilled, the subject circuit would have been acceptable. The present embodiment, however, is desirable because it changes speed gradually, rather than instantaneously. It accomplishes through the utilization of the unique voltage-controlled, pulse modulated circuit of FIG. 12.

When any AND gate output of U4 makes a low-to-high transition, an appropriate capacitor charges linearly. The current flowing into this capacitor is limited by a timing resistor. Higher valued resistors cause the voltage on the capacitors to rise more slowly because the current is restricted to a greater degree. Conversely, when the output of the AND gate of U4 is low, the timing capacitor discharges to zero potential via this same timing resistor. In either case, the subject gradually-varying voltage is utilized to control the duty cycle of the appropriate monostable multivibrator, which, in turn, activates the inputs to the motors.

The output of astable multivibrator U1 is connected to the reset and trigger lines of the monostable multivibrators U2 and U3. This has the effect of repeatedly generating a one-shot timing cycle from the monostable multivibrators. In addition, these multivibrators are configured as voltage-controlled oscillators by varying the voltage level on the voltage control input to these monostable multivibrators. This is accomplished by bufferring the voltage level on the timing capacitors through voltage followers. Accordingly, the duty cycle of the output of the multivibrators is directly proportional to the voltage on the timing capicitors. This provides the desired effect of varying the speed of the motors M1 and/or M2 in direct proportion to the voltage on the timing capacitors of FIG. 12.

As an added precaution, two additional XOR gates are connected directly to the outputs of the four voltage-controlled, monostable multivibrators and to the inputs of the AND gates U5. Similar to the circuitry used at the output of the joystring, this circuit minimizes the drain on the battery by assuring that only one of the two lines for each motor is activated during the interval of time in which the outputs of both monostable multivibrators connected to one motor might be simultaneously high.

The four outputs of AND gate U5 comprise the four motor inputs, that is, two pairs of inputs to each motor. Each motor input is comprised of a pair of the following: a switching NPN transistor, a power NPN transistor connected to the emitter of the switching NPN transistor, and a power PNP transistor connected via a current-limiting resistor to the collector of the switching NPN transistor. The remaining resistors either pull-up or pull-down the voltage level, as appropriate, on the power transistors when the switching NPN transistor is reversed-biased.

A high-level logic signal originating from the output of the AND gate U5 and applied to the base of the switching NPN transistor forward biases both the NPN power transistor connected to the emitter of the switching NPN transistor and the PNP power transistor connected via a current-limiting resistor to the collector of the switching NPN transistor. Provided that the switching NPN transistor on the flip side of the this circuit is reverse biased, the result is to provide differential voltage across the terminals of either motor M1 or M2. It follows that when the duty cycle of the monostable multivibrator that drives the subject switching NPN transistor is near zero, the motor is effectively turned off. When the duty cycle is near 100 percent, the motor is effectively turned full on. Between the 0 and 100 percent duty cycle cases, the motor is effectively turned on at a rate that is proportional to duty cycle at which the appropriate monostable multivibrator is activated.

Furthermore, when two adjacent terminals on the joystring are simultaneously activated, the invention is designed to pivot. While pivoting, one motor is activated in the forward or reverse direction while the other motor is turned off. Tests show that the invention is more effectively controlled if the motors accelerate or decelerate more quickly immediately upon and immediately after a pivot command has been initiated. The present embodiment provides this feature by activating bilateral switches U6 and U7 immediately upon detecting a pivot command. The effect of activating bilateral switch U6 is to reduce the value of the timing resistors and to cause the timing capacitor to charge or discharge more quickly. The effect of activating bilateral switch U7 is to immediately charge a final timing capacitor which will remain high and, thus, continue to activate bilateral switch U6 for a short while after the pivot command was last detected. Accordingly, the motors accelerate or decelerate more quickly whenever the embodiment is in the process of pivoting, as desired.

Figure 13:
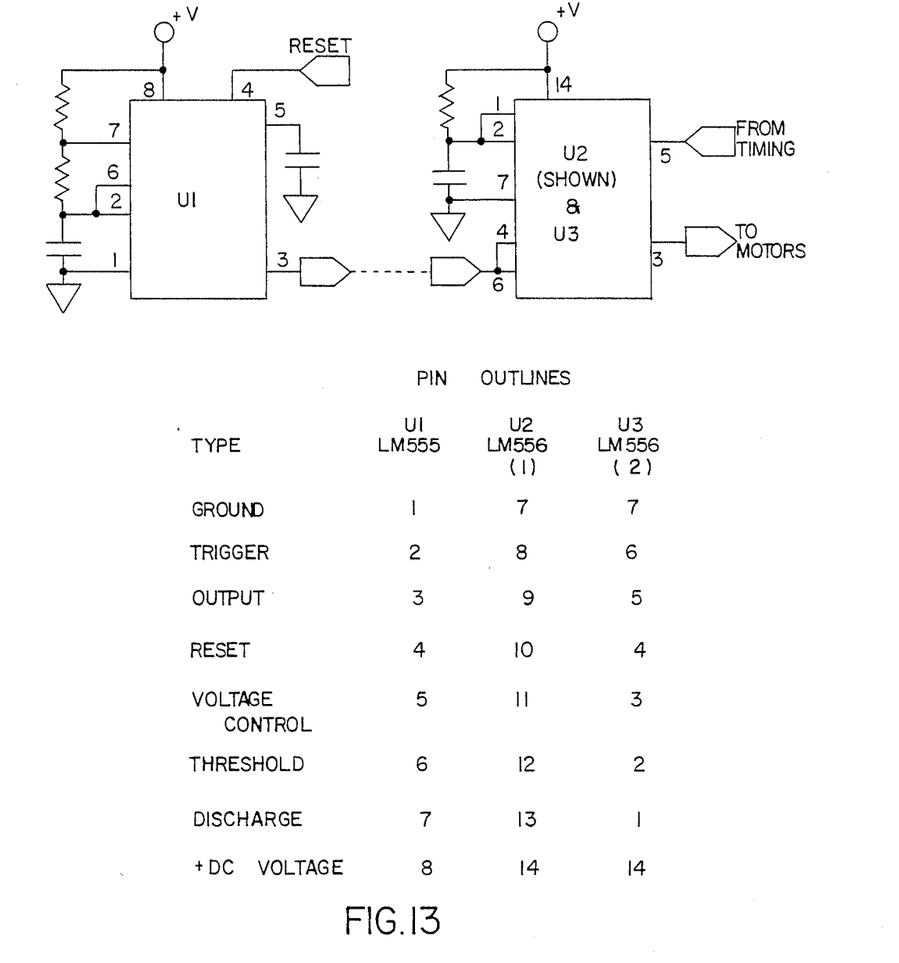

FIG. 13 provides the schematic and pin outlines of U1, U2, and U3 to be used in conjunction with FIG. 12. U1 is a 555 timer IC utilized as an astable multivibrator, although almost any astable multivibrator semiconductor may be used. FIG. 13 also shows the circuitry and pin outlines for U2 and U3 using the 556 timer. (Each 556 timer contains two 555 timers ((one is shown)) and both U2 and U3 utilize the pin outlines shown for the 556 timers.)

The relative height of the invention is adjusted by depresing the rocker-arm type momentary switch 45. The rocker-arm type momentary switch 45 is directly wired to the extension tube drive motor 41 such that by depressing the upper portion of the switch 45 turns the drive motor 41 in the counterclockwise direction and thereby causes the extension tube assembly to expand. Conversely, depressing the lower portion of the switch 45 turns the drive motor 41 in the clockwise direction and causes the extension assembly to contract.

In summary of the operation of the invention as described so far, the momentary switch 45 is used to adjust the height. After this adjustment is complete, the grip ring 17 of the joystring is then pulled in the same direction as the invention is intended to travel and the invention propels itself in such manner as to follow the operator of the invention. As an example of actual use, the height might initally be set to that of a stovetop by depressing the upper or lower portion of the rocker-arm type momentary switch 45, as appropriate. Once the desired height is achieved, the operator releases the momentary switch 45, thus fixing the height of the invention, and begins to load the surface of the invention with the desired meal. The operator then pulls the grip ring 17 with a minimum of effort and walks to a new location, thereby causing the invention to carry the meal to the operator. At the new location, say, a dining room table, the operator continues to guide the invention to be conveniently close to the table and then lowers the serving surface to a height which is convenient for unloading the meal onto the table to be dined from.

Figure 14:
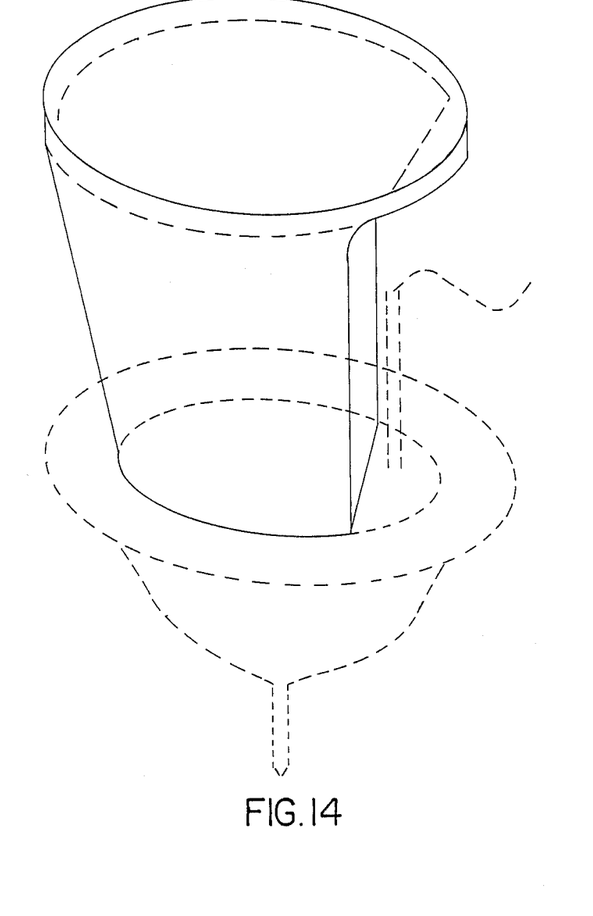
FIG. 14 is a figure showing an attachable laundry basket.

The preferred embodiment of the invention utilizes the attachable laundry basket presented in FIG. 14. The basket would be fabricated from a non-toxic plastic and contoured to fit the serving recesses, thereby restraining the basket against movement while providing the physical clearance necessary for the joystring controller assembly 1 to operate effectively. This laundry basket will be ventilated with holes to facilitate sanitation. By placing soiled clothes into this basket and using the power-elevation feature of the invention, for example, handicapped people would be better able to do their own laundry. Thus, the attachable basket is in keeping with the goal of the invention, which is to help handicapped people improve the quality of their lives by becoming more active and self-sufficient.

Having thus described the preferred embodiment of the present invention in detail, it is intended to be understood that many embodiments thereof will suggest themselves without departing from the spirit and scope of this invention. For example, skilled artisans will readily be able to change the dimensions and shapes of the various embodiments. They will be able to make the invention from other plastics and/or alternative materials, such as metal. They may eliminate the concept of the powered height adjustment or replace it with a manual height adjustment mechanism. They can reconfigure the invention to make it capable of carrying a specific object, which may be heavier or lighter than the load-carrying capability of the present embodiment. They can make many adjustments to the electronic circuitry, such as using instantaneous or non-linear motor acceleration techniques. Or, they may replace the electronic circuitry with other semiconductor-based components, including computers, to control the operation of the motors and/or replace the joystring assembly with remote-sensing detectors, such as (but not limited to) infra-red, radio-wave, or sonar. Perhaps most importantly, the concept of the present embodiment can be utilized to create, say, a child's toy or one of many tools to be used commercially or in industry. Accordingly, it is intended that the specification and drawings be interpreted as illustrative rather than a limited sense.

What is claimed is:

1. A machine for use by a partially invalid or handicapped or walking-assistance-dependent person, for transporting objects and following the person within an interior living space, comprising:
   (a) propelling means for propelling said machine, including wheels adapted only for use in said interior living space;
   (b) carrying means for carrying objects to be transported;
   (c) control means for detecting the approximate position of said machine relative to the person using said machine and for activating the propelling means; and
   (d) digital electronic circuitry means connected to the control means and effective to cause said machine to propel itself in the approximate direction of said person using the machine in any and all orientations of the user person with respect to the front, sides and rear of the machine,
   said control means including separate contacts for respective forward, right, rear and left drive, and said control means including joystring post means for engaging and activating said contacts responsive to the direction in which said joystring post means is pulled;
   said control means including an elastic stretchable joystring attached to said joystring post means and at least indirectly to the person,
   and said digital electronic circuitry means including means for effecting gradual acceleration and deceleration of the machine to avoid tipping of the machine or spilling of liquids carried on the machine;
   whereby the person can walk forward at varying rates and can make turns and the machine will closely follow the person, carrying said objects for the convenience of the person.

2. The apparatus of claim 1 wherein said digital circuitry means include a voltage controlled, pulse modulated circuit effective to cause the propelling means to accelerate gradually, serving as said means for effecting gradual acceleration.

3. The apparatus of claim 1 including height means for adjusting the height of said carried objects relative to the surface upon which said apparatus is being propelled.

4. The apparatus of claim 3 wherein said height means comprise a plurality of tubular sections telescoped into one another.

5. The apparatus of claim 1 wherein said machine is comprised of two components separated by a common vertical assembly.

6. The apparatus of claim 5 wherein said carrying means include a contoured surface whereby objects are restrained from moving freely upon.

7. The apparatus of claim 6 wherein the edge of said contoured surface is protected with a soft material and padded.

* * * * *